United States Patent
Hellmich et al.

(10) Patent No.: US 9,733,160 B2
(45) Date of Patent: Aug. 15, 2017

(54) METHOD FOR EMBEDDING A BIOLOGICAL SAMPLE IN A TRANSPARENT MATRIX FOR ANALYSIS USING SINGLE PLANE ILLUMINATION MICROSCOPY

(71) Applicant: Carl Zeiss Microscopy GmbH, Jena (DE)

(72) Inventors: Wibke Hellmich, Jena (DE); Benno Radt, Jena (DE); Helmut Lippert, Jena (DE); Olaf Selchow, Jena (DE); Uwe Wolf, Magdala (DE); Juergen Haese, Kahla (DE)

(73) Assignee: Carl Zeiss Microscopy GmbH, Jena (DE)

( * ) Notice: Subject to any disclaimer, the term of this patent is extended or adjusted under 35 U.S.C. 154(b) by 57 days.

(21) Appl. No.: 14/132,988

(22) Filed: Dec. 18, 2013

(65) Prior Publication Data

US 2014/0202265 A1    Jul. 24, 2014

Related U.S. Application Data

(63) Continuation of application No. 12/997,113, filed as application No. PCT/EP2009/004081 on Jun. 6, 2009, now abandoned.

(30) Foreign Application Priority Data

Jun. 11, 2008 (DE) .................. 10 2008 027 784

(51) Int. Cl.
*G01N 1/28* (2006.01)
*G02B 21/32* (2006.01)
*G02B 21/34* (2006.01)

(52) U.S. Cl.
CPC ............... *G01N 1/28* (2013.01); *G02B 21/32* (2013.01); *G02B 21/34* (2013.01)

(58) Field of Classification Search
CPC ........... G01N 1/28; G02B 21/32; G02B 21/34
See application file for complete search history.

(56) References Cited

FOREIGN PATENT DOCUMENTS

DE         102 57 423      6/2004
WO    WO 2004/053558      6/2004

OTHER PUBLICATIONS

K. Greger et al., "Basic building units and properties of a fluorescence single plane illumination microscopy", Review of Scientific Instruments, vol. 78, No. 2, Feb. 28, 2007, pp. 23705-23705, XP012103772.

(Continued)

*Primary Examiner* — Sam P Siefke
(74) *Attorney, Agent, or Firm* — Haug Partners LLP

(57) ABSTRACT

The invention is directed to method for positioning and aligning a preferably biological sample in the detection area of the objective of a microscope arrangement. According to the invention, the method mentioned above has the following method steps: a sample is introduced into a transparent medium, preferably agarose gel, which is initially liquid; the medium is changed from the liquid state to the solid state, wherein the sample is fixated within the medium, but the transparency of the medium is retained; the solidified medium is positioned in the microscope arrangement in such a way that the sample enclosed therein is situated in the detection area of the objective. Further, a device is proposed for positioning and aligning a preferably biological sample in the detection area of the objective of a microscope arrangement.

2 Claims, 6 Drawing Sheets

(56) References Cited

OTHER PUBLICATIONS

S. Preibisch et al., "Towards digital representation of *Drosophila embryogenesis*", Biomedical Imaging: From Nano to Macro, 2008, ISBI 2008. $5^{th}$ IEEE International Symposium ON, IEEE, Piscataway, NJ, USA, May 14, 2008, pp. 324-327, XP031271042.
Christoph J. Engelbrecht et al., Resolution enhancement in a light-sheet-based microscope (SPIM), Optics Letters, May 15, 2006, vol. 31, No. 10.
Jan Huisken et al., "Optical Sectioning Deep Inside Live Embryos by Selective Plane Illumination Microscopy", Science, Aug. 13, 2004, vol. 305, pp. 1007-1009.
Notification of Transmittal of Translation of the International Preliminary Report on Patentability dated Jan. 20, 2011.

METHOD FOR EMBEDDING A BIOLOGICAL SAMPLE IN A TRANSPARENT MATRIX FOR ANALYSIS USING SINGLE PLANE ILLUMINATION MICROSCOPY

The present application is a continuation of U.S. patent application Ser. No. 12/997,113 filed on Dec. 9, 2010, which claims priority from PCT Patent Application No. PCT/EP2009/004081 filed on Jun. 6, 2009, which claims priority from German Patent Application No. DE 10 2008 027 784.3 filed on Jun. 11, 2008, the disclosures of which are incorporated herein by reference in their entirety.

BACKGROUND OF THE INVENTION

1. Field of the Invention

The invention is directed to a method and a device for positioning and aligning a preferably biological sample in the detection area of the objective in a microscope arrangement.

The method according to the invention can be applied particularly in connection with single plane illumination microscopy (SPIM). This microscopy method is a special method of widefield microscopy by which image data for a three-dimensional image of the sample are obtained on the basis of optical sections through different planes of the sample.

2. Description of Related Art

SPIM technology is described, for example, in Stelzer et al., Optics Letter 31, 1477 (2006), Stelzer et al., *Science* 305, 1007 (2004), DE 102 57 423 A1, and WO 2004/0530558 A1.

The viewing direction on the sample is changed repeatedly so that image data are not obtained from just one viewing direction on the sample. Every time the viewing direction is readjusted, the sample must be positioned and aligned relative to the detection objective.

At present, the positioning and alignment of the sample to be examined is carried out manually using commercially available equipment and is therefore extremely time-consuming and is accordingly only suitable for laboratory analyses of individual samples.

However, particularly with regard to high volumes in industrial applications, there is an increasing demand for detection of a large number of samples successively in time with the highest possible throughput per time unit.

SUMMARY OF THE INVENTION

Therefore, it is the object of the invention to propose a method and at least one device by which it is possible to position and align samples in the detection area of a microscope arrangement with high efficiency. By the word positioning is meant within the meaning of the invention the arrangement of the sample in the detection area of the objective, while the word alignment refers to the respective viewing direction of the objective on the sample.

According to the invention, the following method steps are carried out in a method of the type mentioned above:
the sample is introduced into a transparent medium which is initially in liquid state,
the medium is changed from the liquid state to a solid state so that the sample is fixated inside the medium, but the medium remains transparent or the transparency changes only negligibly,
the solidified medium is positioned in the microscope arrangement in such a way that the sample enclosed therein is situated in the detection area of the objective.

In a first preferred embodiment of the invention, a plurality of samples are introduced into the transparent medium which is initially still in a liquid state. The medium with the samples contained therein is stored in a sample reservoir.

When one of the samples is to be examined, a partial amount of the transparent medium which is still in liquid state is removed from the sample reservoir with the sample to be examined. After being removed, the partial amount of medium is changed from liquid to solid state, and the sample is fixated within the solidifying partial amount of medium.

A partial amount can also be removed with a plurality of selected samples. After removal, this partial amount of the medium is changed from the liquid state to the solid state, and the samples are fixated within the solidified partial amount of medium.

The partial amount of medium is removed from the sample reservoir, for example, in that it is sucked into the hollow space of a capillary or cannula or, for example, into the hollow space of a disposable medical syringe.

By capillary is meant within the meaning of the present invention a hollow needle with a very small inner diameter and a suction and delivery piston which is displaceably guided in the interior; a suction effect is achieved when the suction and delivery piston is displaced in one direction so that a partial amount of the liquid medium is removed from the reservoir, while the medium with the enclosed sample is pushed out of the capillary when the suction and delivery piston is displaced in the opposite direction.

By cannula is meant within the meaning of the invention a hollow needle with an inner diameter greater than that of the capillary and, consequently, without capillary action. A displaceable suction and delivery piston can likewise be provided in the interior of the cannula for the purpose described above.

A suction and delivery piston which can be used to suck in or push out a partial amount of medium is likewise provided in the, usually cylindrical, hollow space of the disposable syringe.

In a method step following the fixating of the sample, the solidified medium is held in the microscope arrangement in such a way that the sample fixated therein is situated in the detection area. For this purpose, at least that portion of the solidified medium in which a sample is located is pushed out of the hollow space into the detection area. The portion of medium that is not pushed out remains in the hollow space and is held therein, and the alignment and position of the sample in the detection area is influenced in a desired manner by means of specific changes in the position of the capillary, cannula or disposable syringe.

If there are a plurality of enclosed samples, the medium is held in the microscope arrangement in such a way that one of the samples enclosed therein is initially situated in the detection area, and after this sample has been examined the next sample located in the partial amount is positioned and aligned and can be examined.

In a second preferred embodiment of the invention, the transparent medium which is still in the liquid state is stored in a medium reservoir without samples.

In contrast to the first embodiment of the invention:
a partial amount of the medium which does not yet contain a sample is initially introduced into the hollow space of a capillary, a cannula or a disposable syringe in a first step, and
one or more samples are introduced into the medium already located in the hollow space in a second step.

The inventive idea includes different ways of carrying out the method: For example, it is conceivable to carry out both of the above-mentioned steps directly one after the other in that the medium in the liquid state is introduced first and, immediately following this, the sample is introduced into the medium which is still in the liquid state. This can be carried out with just a sample by itself or also with a sample which is already embedded in a smaller partial amount of the medium.

When a disposable syringe is used, for example, the liquid medium can be introduced first and then one or more samples can be introduced into the cylindrical hollow space of the disposable syringe making use of gravitational force.

In contrast to this, it can also be provided that:
the medium introduced in the hollow space is first changed from the liquid state to the solid state in an intermediate step before introducing the samples, or
a partial amount of the medium which is in the solid state is introduced into the hollow space, and
the medium in the hollow space is not liquefied again until a later time,
the sample is introduced, and
the medium is solidified again in order to fixate the sample therein.

This way of carrying out the method can be used advantageously in connection with preparing a plurality of samples which are already fixated prior to microscopic examination.

In each of the cases mentioned above, the solidified medium is pushed out of the hollow space in order to position and align a sample fixated therein in the detection area of the objective of a microscope arrangement.

The change of the medium from the liquid state to the solid state, or vice versa, is carried out under external influences, particularly by heating or cooling. The solidification of the medium can also be carried out under the influence of light.

Further, an automation of the method steps in their entirety or an automation of some of the individual method steps lies within the scope of the invention.

A curable gel, preferably agarose gel, is used as medium.

The invention is further directed to a device for positioning and aligning a preferably biological sample in the detection area of an objective of a microscope arrangement comprising:
a reservoir for a transparent medium which is initially still liquid,
means designed for
removing a partial amount of the liquid medium and for introducing a sample in this partial amount, or
introducing samples into the liquid medium inside the reservoir and removing a partial amount of the medium with a sample contained therein,
means for changing the removed partial amount of medium from the liquid state to the solid state, at least one sample being fixated within the partial amount of the medium, and
a device for positioning and aligning the solidified partial amount of medium in the microscope arrangement in such a way that a sample contained therein is situated in the detection area of the objective.

The device is advantageously outfitted with a manipulating unit which has a capillary, a cannula or a disposable medical syringe in which a suction and delivery piston is movably guided. Small volumes can be sucked in by displacing the piston and by the vacuum pressure generated in this way. Accordingly, it is possible to remove a partial amount on this order of magnitude from the total reservoir of still liquid medium in a precise manner.

The manipulating unit will be explained more fully referring to the example of capillaries, although the invention is not limited to this.

For example, the manipulating unit can be designed to receive a plurality of capillaries simultaneously. This proves advantageous when a set of samples is prepared and distributed to a plurality of capillaries, which samples are received by the manipulating unit and exchanged with one another in a simple manner, so that the samples received therein can be examined efficiently one after the other in rapid sequence.

For the purpose of exchanging the capillaries in the sample space, the manipulating unit can be outfitted with a turret arrangement receiving the capillaries. Accordingly, one of the capillaries is moved into a position in which the suction and delivery piston is grasped and the portion of the medium with the enclosed sample is pushed into the detection area by means of the suction and delivery piston. After being examined, the sample is pulled back into the capillary by the suction and delivery piston and is stored therein, the next capillary with the next sample is moved into position, the suction and delivery piston is grasped, and this sample is now pushed into the detection area.

In this connection, it is advantageous when the suction and delivery piston comes into contact with the medium directly (i.e., without an air cushion) so as to facilitate metering of a highly viscous medium such as a gel in particular. Further, this prevents unwanted substances being sucked in via the air cushion (e.g., in the form of aerosols) which is important above all when handling living biological samples.

In a particularly advantageous embodiment of the arrangement according to the invention, the capillary, including the suction and delivery piston guided therein, is connected to the manipulating unit by connection elements which can be disconnected manually. In so doing, the capillary can also be located in a sleeve which is then connected to the manipulating unit.

In this way, it is possible to disconnect the capillary, including the suction and delivery piston guided therein, from the manipulating unit, to immerse the suction opening of capillary in the medium, to displace the suction and delivery piston in the capillary, and to suck a partial amount of medium into the capillary corresponding to a predetermined volume.

Depending on one of the modes of carrying out the method which have already been described, the sucked in medium can already contain a sample, or a sample is introduced subsequently in the partial amount of medium located in the capillary.

When the medium and the sample are located in the capillary, the medium is changed from the liquid state to the solid state with the means according to the invention provided for this purpose in order to fixate the sample within the partial amount of medium as will be described in more detail below with reference to an embodiment example.

The capillary which now contains the solid medium and the sample enclosed therein is subsequently arranged at the manipulating unit again by means of the connection elements.

The manipulating unit, per se, is fastened to the microscope arrangement (e.g., by means of a straight-line guide) and it is outfitted with means for changing the position and alignment of the capillary relative to the microscope arrangement, wherein there is a change in position of the capillary in coordinates X, Y, Z and a rotational movement around the longitudinal direction of the capillary by an angle φ.

With the manipulating unit it is possible to move the end portion of the capillary in which the sample is located into the vicinity of the detection area initially by means of displacement in coordinates X and Y and then, using the suction and delivery piston, to push the solidified medium with the enclosed sample out of the capillary in direction of coordinate Z until the sample is positioned in the detection area. By rotating the sample around angle φ, the alignment of the sample (i.e., the viewing direction of the objective on the sample positioned in the detection area) is varied in the desired manner.

It lies within the scope of the invention to directly manually initiate the movements of the capillary by means of correspondingly constructed gear unit members and also to initiate these movements by controlling motorized drives to which the capillary is connected by gear unit members.

DETAILED DESCRIPTION OF EMBODIMENTS

It is to be understood that the figures and descriptions of the present invention have been simplified to illustrate elements that are relevant for a clear understanding of the present invention, while eliminating, for purposes of clarity, many other elements which are conventional in this art. Those of ordinary skill in the art will recognize that other elements are desirable for implementing the present invention. However, because such elements are well known in the art, and because they do not facilitate a better understanding of the present invention, a discussion of such elements is not provided herein.

The present invention will now be described in detail on the basis of exemplary embodiments.

Figure 1:
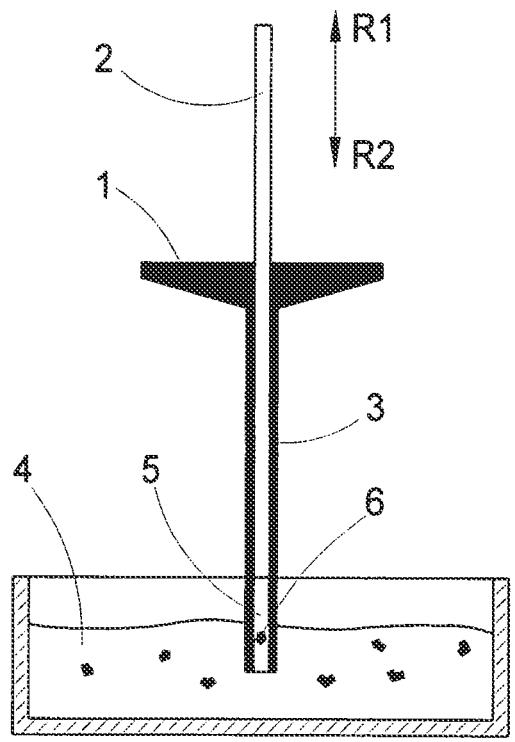
FIG. 1 shows a capillary with a suction and delivery piston guided so as to be movable in its interior and a sample reservoir in which the end portion of the capillary is immersed.

FIG. 1 shows a capillary 1 with a suction and delivery piston 2 which is guided in the interior so as to be displaceable in directions R1 and R2. Combinations of capillaries 1 and suction and delivery pistons 2 of this kind are known, per se, as pipettes and are used for dispensing liquids.

The capillary 1 can be made of glass or plastic and can be provided with a volume scale (not shown in the drawing) arranged laterally in longitudinal direction. The suction and delivery piston 2 is generally made of a flexible plastic, but can also be formed of a stainless steel rod linkage with a plunger arranged thereon.

When the end portion 3 of the capillary 1 is dipped into a sample reservoir 4 in which a transparent, initially liquid medium in the form of agarose gel 5 and a plurality of samples 6 are located and the suction and delivery piston 2 is displaced inside the capillary 1 in direction R1, a partial amount of the agarose gel 5 of for example, about 30 μL to 50 μL is sucked into the capillary 1 and this partial amount of agarose gel 5, including one of the samples 6, is removed from the total reservoir of samples 6 in a precise manner.

Figure 2:
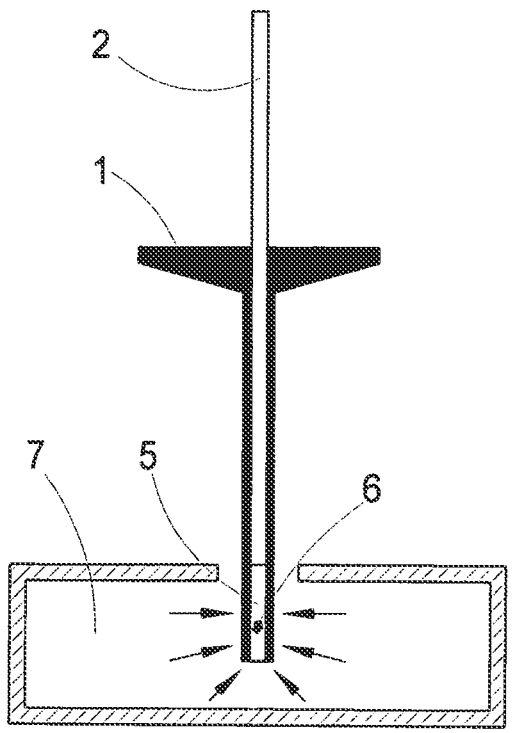
FIG. 2 shows the capillary according to FIG. 1 in a curing station, shown schematically, in which heat energy is extracted from a transparent medium which is initially still in liquid state in order to solidify it.

The sample 6, surrounded by the agarose gel 5 which is likewise removed, is transported by the capillary 1 to a curing station 7, shown schematically in FIG. 2, where the agarose gel 5 is cooled. The agarose gel 5 is increasingly solidified as heat energy is extracted while remaining transparent, and the sample 6 is fixated in the agarose gel 5.

Figure 3:
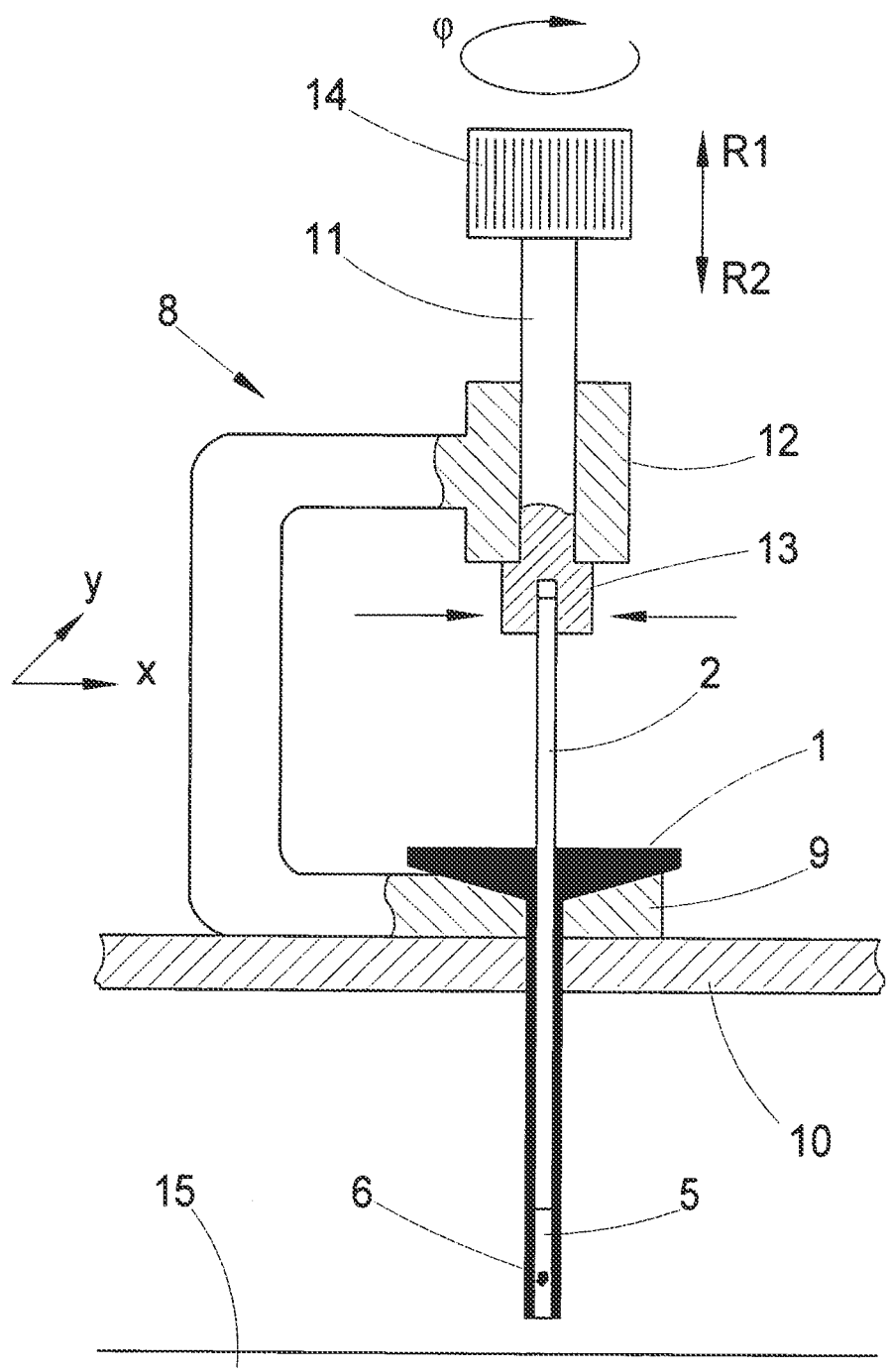
FIG. 3 shows a schematic illustration of the mode of operation of a manipulating unit designed for positioning and aligning a sample in the detection area of a microscope objective.

The capillary 1 with the sample 6 fixated in the agarose gel 5 is now transported to a manipulating unit 8, shown schematically in FIG. 3, and fixed therein by means of a receptacle 9. The manipulating unit 8 is in turn fastened to a microscope stand 10, only a partial area of which is shown for the sake of clarity.

It is advantageous when a connection of the manipulating unit 8 to the microscope stand 10 is provided by means of straight-line guides which ensure a displacement of the manipulating unit 8 relative to the microscope stand 10 in coordinates X and Y.

The manipulating unit 8 is outfitted with an actuating element 11 which is supported in a rotating and straight-line guide 12 and is accordingly displaceable in directions R1 and R2 and rotatable around an angle φ. The directions R1 and R2 extend parallel to coordinate Z in coordinate system X, Y, Z.

The actuating element 11 has a clamping device 13 which encloses the end of the suction and delivery piston 2 remote of the sample 6. The clamping device 13 causes displacements of the actuating element 11 in directions R1 and R2 and also the rotation of the actuating element 11 to be transmitted to the suction and delivery piston 2. A drive element 14 serves to initiate the displacements in directions R1 and R2 and the rotational movement.

After the capillary 1 is locked in the manipulating unit 8 and the clamping connection between the suction and delivery piston 2 and the actuating element 11 is produced, the sample 6 is located in the vicinity of the detection area which is represented here by the illumination beam path 15 in the form of a light sheet which is formed and provided for subsequent examination of the sample 6 by the method of single plane illumination microscopy (SPIM).

Before starting the examination, it must be ensured that the sample 6 is situated in the illumination beam path 15. To achieve the configuration shown in FIG. 4, the actuating element 11 is displaced in direction R2 by the rotational movement of the drive element 14 based on the diagram shown in FIG. 3, and the displacing movement is transmitted by means of the clamping device 13 to the suction and delivery piston 2 and then to the agarose gel 5 with the sample 6 enclosed therein.

Figure 4:
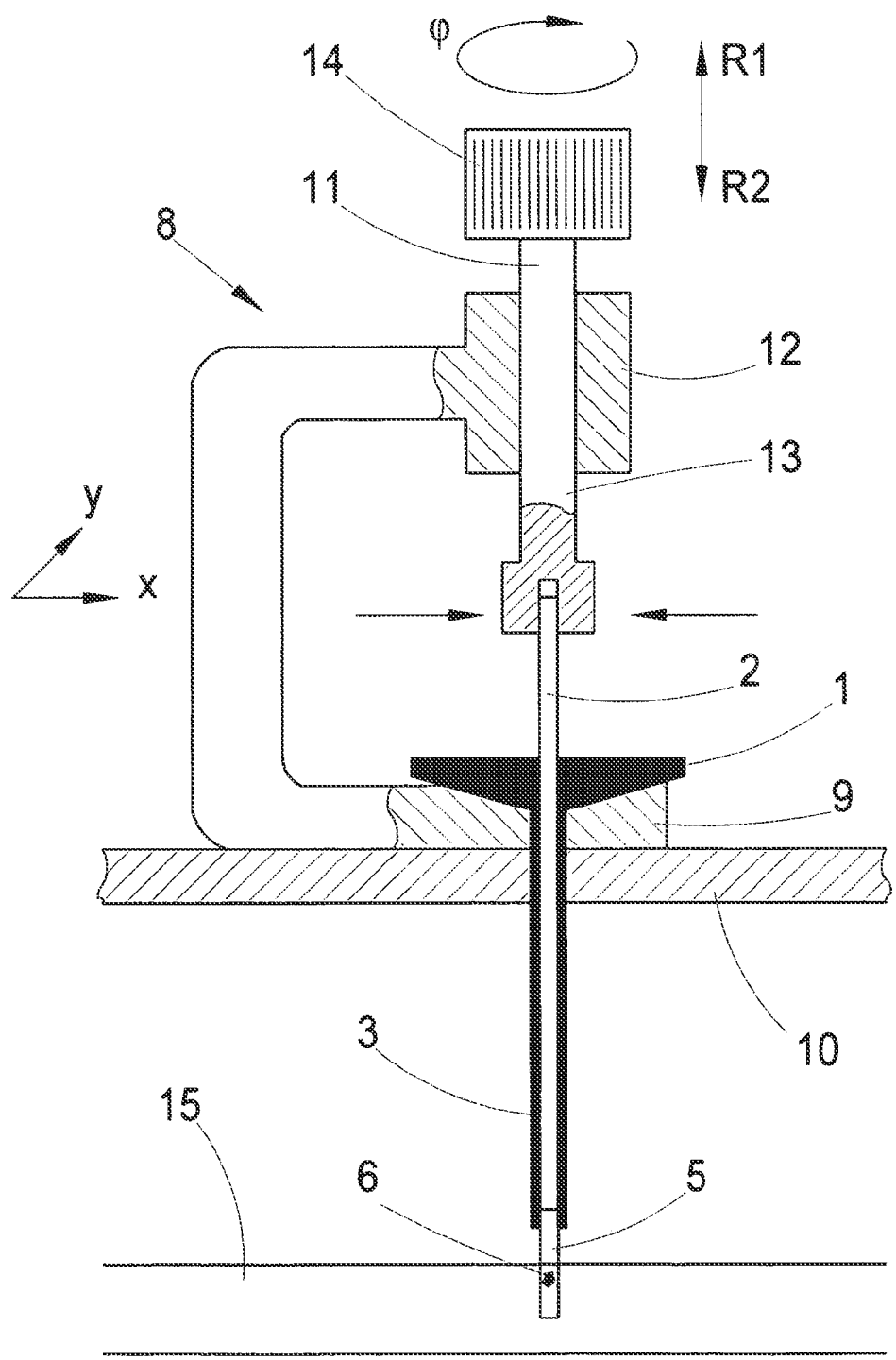
FIG. 4 shows the manipulating unit according to FIG. 3, wherein the sample is positioned in the illumination beam path of a microscope and is aligned on the sample in a first viewing direction of the microscope objective on the sample.

Since the capillary 1 is not included in this displacing movement because it is locked in the manipulating unit 8, the agarose gel 5 with the sample 6 is pushed out of the capillary 1 until the configuration illustrated in FIG. 4 is achieved and the sample 6 is situated in the illumination beam path 15.

The detection direction of the microscope objective, not shown in the drawing, is perpendicular to the drawing plane. By rotating the capillary 1 by an angle φ within a range of 360 degrees, the detection direction relative to the sample 6 can be changed as needed.

In this way, the positioning and alignment of samples 6 in the illumination beam path 15 and detection area of the microscope, respectively, can always be reproduced.

A first variant for filling the capillary 1 was described with reference to FIG. 1. An alternative variant which satisfies the demand for increased throughput per time unit in the examination of samples 6 is shown by way of example in FIG. 5.

In this case, a filling station 16 is provided in which an empty capillary 1 is initially inserted. The filling station has an access 17 for agarose gel 5 and an access 18 for samples 6. Further, a guide 19 is provided for a piston 22 in order to displace the latter in a straight line in directions R1 and R2. The filling station is preferably combined with a curing station possessing possibilities for temperature control and for supplying and removing heat.

Valves 20 and 21 which are preferably electronically controllable and are alternately opened and closed depending on the control are arranged in accesses 17 and 18.

The filling station 16 is operated in such a way, for example, that the valve 20 is initially open and liquid agarose gel 5 is displaced through the access 17 until it is below the piston 22 and is displaced farther into the capillary in direction R2.

The agarose gel 5 is pressed in direction R2 into the capillary 1 or sinks (for example, when the piston 22 is removed) into the capillary 1 under the influence of gravitational force or capillary force. To prevent the agarose gel 5 from flowing out through the lower end of the capillary 1, a closure 23 is placed on this end as soon as agarose gel 5 is located in the capillary 1. The valve 20 is then closed.

Valve 21 is now opened and a sample 6 is displaced through access 18 until it is below the piston 22 and is displaced farther into the capillary in direction R2.

After valve 21 is closed, the valve 20 is opened again, if required, and liquid agarose gel 5 is again fed through access 17.

Alternatively, instead of supplying a sample 6 by itself, a sample 6 which is already embedded in a partial amount of agarose gel 5 can be fed through access 18. This partial amount is then pressed into the capillary 1 along with the embedded sample 6 by means of the piston 22 or sinks into the capillary 1 under the influence of gravitational force and combines with the agarose gel 5 already located therein.

Subsequently, the valves are closed and the piston 2 is displaced in direction R2 so that it contacts the agarose. After the agarose cures, the sample can be moved up and down by rotating the drive element 14.

It is advantageous when the upper opening of the capillary 1 (i.e., the opening of the capillary 1 opposite the direction of gravitational force) is conically expanded so that the agarose gel 5 can flow into the capillary 1 more reliably (not shown in the drawing).

Figure 5:
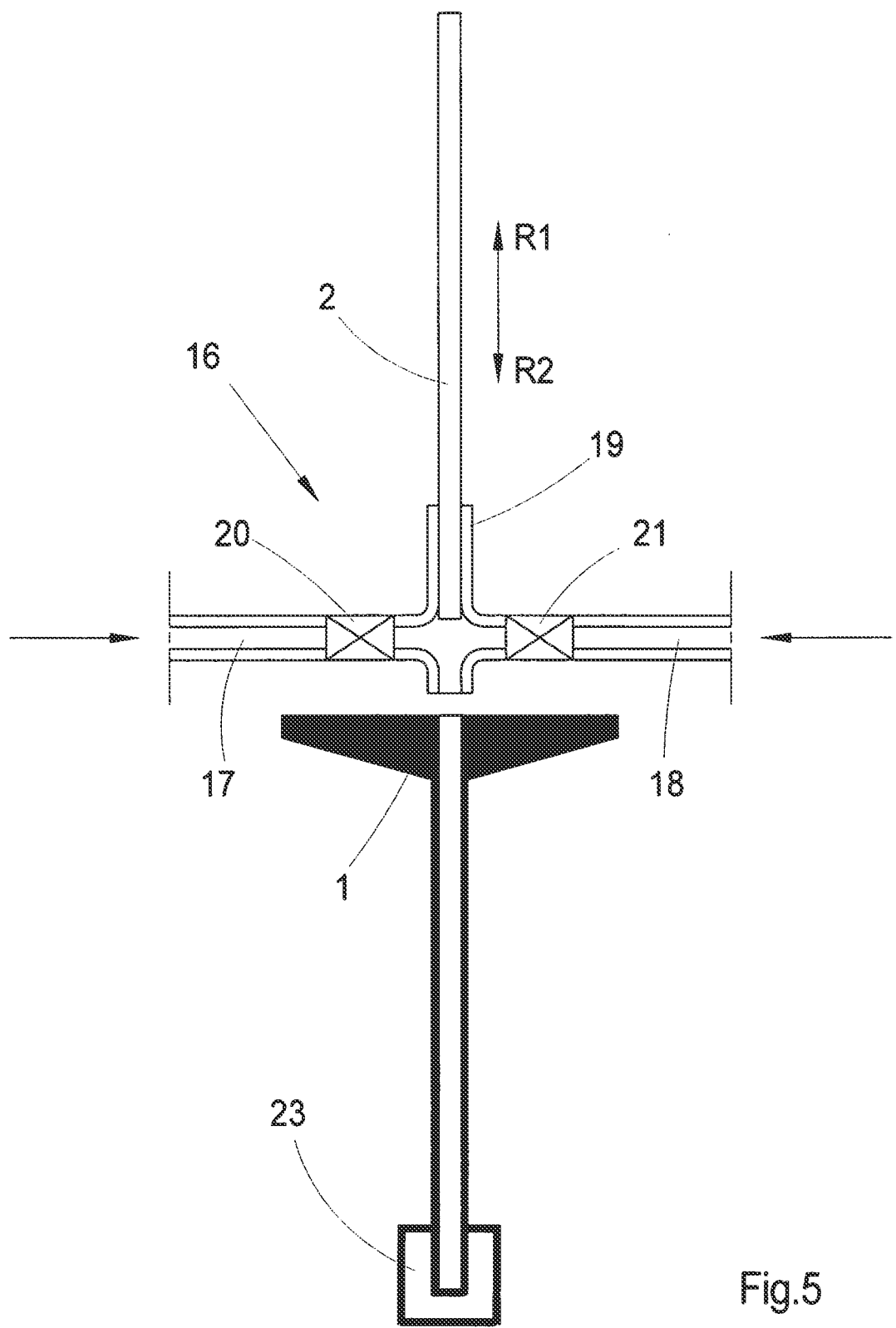
FIG. 5 shows an alternative example for introducing samples into a capillary shown in FIG. 1.
Figure 6:
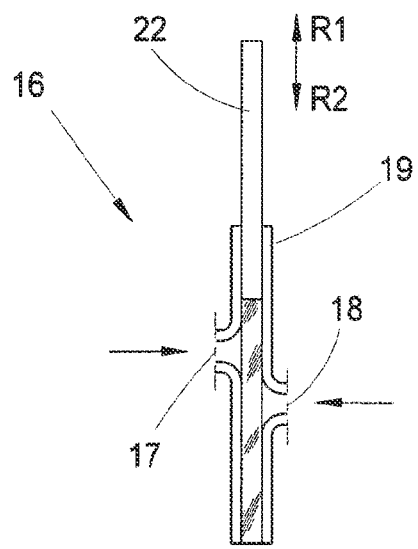
FIGS. 6 to 8 show another example for introducing individual samples into a curable medium.

It also lies within the scope of the invention to construct the filling station in the manner shown in FIG. 6. Filling with agarose gel 5 is accordingly initially carried out as described above. However, the rounded or otherwise shaped end of a tool guided through access 18 is then pressed into the agarose gel 5 which is still in liquid state, whereupon the agarose gel 5 is cured, and the tool is removed again after curing so that a depression 24 (e.g., in the shape of a hollow cone or a trough) remains in the cured agarose gel 5. The valves are not shown in FIG. 6 for the sake of clarity, especially since their function has already been described referring to FIG. 5.

Figure 7:
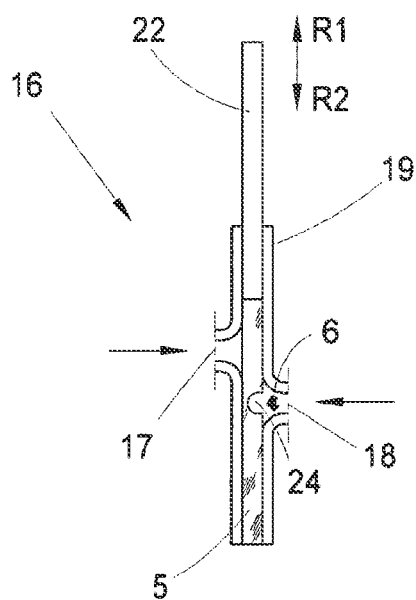

After the tool has been removed, a sample 6 is advanced into the depression 24 through access 18 as is indicated in FIG. 7. Just the sample by itself or the sample located in a partial amount of agarose can be supplied. If required, an additional partial amount of agarose is introduced.

Figure 8:
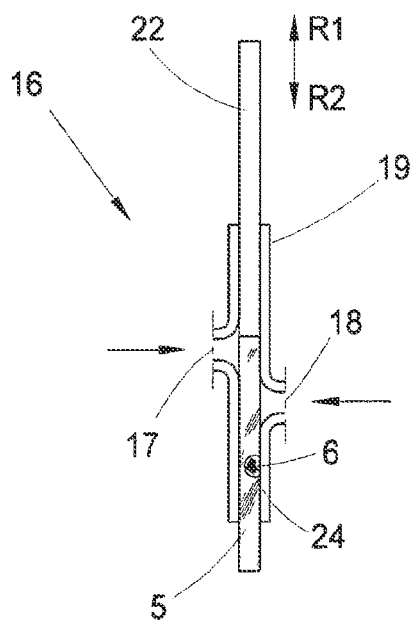

When the sample 6 has been advanced into the depression 24, the agarose gel 5, including the sample 6 located in the depression 24, is advanced by the piston 2 until the configuration shown in FIG. 8 is achieved. If required, the agarose gel 5 is now liquefied again by temporarily supplying heat in order to embed the sample 6 completely in the agarose gel 5.

It is advantageous when the filling station is designed so as to be compatible with a microscope so that the sample can be inserted in the depression 24 and oriented while being observed.

Subsequently, the same process as that described referring to FIG. 5 may be carried out, wherein the capillary 1 is removed from the filling station 16 and is prepared for microscopic examination as was described above with reference to FIG. 3 and FIG. 4.

It is advantageous when the filling station and the manipulating unit form a functional unit.

Figure 9:
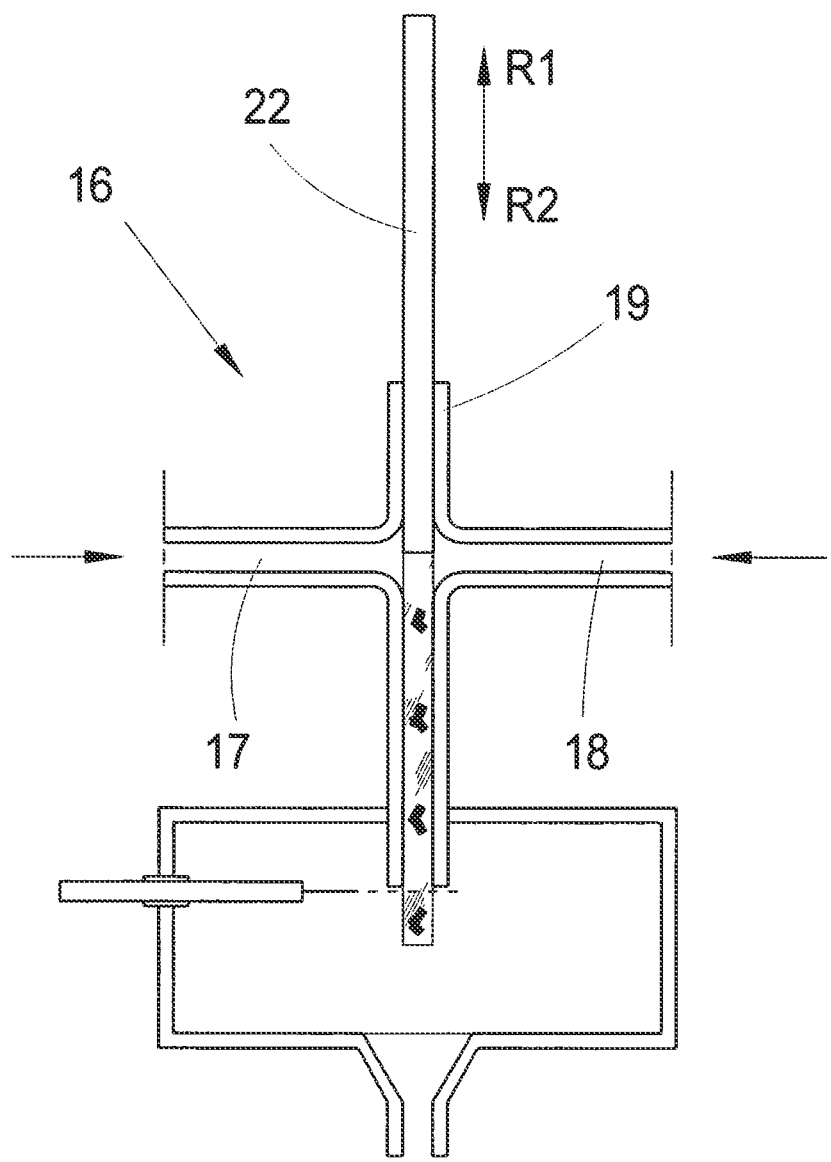
FIG. 9 shows an example for a timed introduction of a plurality of samples into a curable medium.

However, the inventive idea also includes a mode of operation for filling capillaries or cannulas which expands on the mode of operation described with reference to FIGS. 6 to 8. The following description refers to FIG. 9.

The following is carried out at given time intervals:
a first sample 6.1 is introduced into the agarose gel 5,
the agarose gel 5 is advanced with the piston 22,
a second sample 6.2 is introduced into the agarose gel 5,
the agarose gel 5 is advanced again,
a third sample 6.3 is introduced, and so on, until a given quantity n of samples 6.$n$ have been inserted in the agarose gel 5, wherein distances a are adjusted between the samples 6.1, 6.2, . . . , 6.$n$ depending on the timing and forward feed speed.

In this case, the agarose gel 5 is solidified by extracting heat at position P with the same timing with which the samples 6.1, 6.2, . . . , 6.$n$ are embedded in the agarose gel 5, and the sample 6.2 located at position P is accordingly fixated in the agarose gel 5.

The samples 6 can subsequently be examined microscopically as was described above.

A portion A of the agarose gel 5 in which a sample (e.g., sample 6.1 in this instance) is embedded is severed by means of a cutting device 26 which is guided through the housing wall of the curing station 25 and provided with a knife 27 which is displaceable in directions S1 and S2.

The severed portion falls through a funnel-shaped opening 28 out of the curing station 25 under the influence of gravitational force and can be supplied for further analytic methods.

It is noted that the suction and delivery piston 2 and the piston 22 described in the embodiment examples have different functions inasmuch as the piston 22 has no suction function, which is achieved, for example, in that it is guided with a sufficiently large play in the hollow cylinder. Nevertheless, the piston 22 can be exchanged for a suction and delivery piston 2 insofar as the corresponding function is desired for handling the agarose gel 5 and sample 6.

While this invention has been described in conjunction with the specific embodiments outlined above, it is evident that many alternatives, modifications, and variations will be apparent to those skilled in the art. Accordingly, the preferred embodiments of the invention as set forth above are intended to be illustrative, not limiting. Various changes may be made without departing from the spirit and scope of the inventions as defined in the following claims.

REFERENCE NUMBERS 1 capillary
2 suction and delivery piston
3 end portion
4 sample reservoir
5 agarose gel
6 sample
7 curing station
8 manipulating unit
9 receptacle
10 microscope stand
11 actuating element
12 rotating and straight-line guide
13 clamping device
14 drive element
15 illumination beam path
16 filling station
17, 18 access
19 straight-line guide
20, 21 valve
22 piston
23 closure
24 depression
25 curing station
26 cutting device
27 knife
28 opening
R1, R2 directions
φ angle
a distance
A portion
P position

The invention claimed is:

1. A device for introducing a sample into a detection area of an objective of a microscope arrangement, comprising:
a reservoir for a transparent medium which is initially still liquid;
a needle-piston unit comprising:
a hollow needle; and
a suction and delivery piston which is movably guided in the needle for sucking a partial amount of the medium into the hollow needle or ejecting it from the hollow needle; and
a manipulating unit comprising:
a receptacle configured to receive the needle-piston unit; and
a connection portion configured to connect to a holder of the microscope arrangement;
wherein the manipulating unit is configured to manipulate the needle-piston unit so as to:
position and align the partial amount of medium, after the partial amount of medium is solidified within the needle, in the microscope arrangement in such a way that a sample contained in the solidified partial amount of medium is situated in the detection area of the objective; and
change a position of the sample along a coordinate X, a coordinate Y, and a coordinate Z; and
rotate the sample around a longitudinal direction of the hollow needle by an angle φ;
wherein the needle-piston unit is fastened to the manipulating unit by means of connection elements configured to be manually disconnected from the hollow needle;
wherein the hollow needle of the needle-piston unit is in the form of a capillary or a cannula.

2. The device according to claim 1, further comprising:
a means for introducing the sample into the partial amount medium after the partial amount of medium is arranged in the needle.

* * * * *